(12) United States Patent
Hofstetter et al.

(10) Patent No.: US 12,327,489 B2
(45) Date of Patent: Jun. 10, 2025

(54) SUTURING SKILLS SURGICAL TRAINING MODEL

(71) Applicant: Applied Medical Resources Corporation, Rancho Santa Margarita, CA (US)

(72) Inventors: Gregory K. Hofstetter, Rancho Santa Margarita, CA (US); Brian Carter, Columbia, MD (US); Oscar Raygan, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 187 days.

(21) Appl. No.: 17/986,441

(22) Filed: Nov. 14, 2022

(65) Prior Publication Data

US 2023/0070953 A1 Mar. 9, 2023

Related U.S. Application Data

(63) Continuation of application No. 16/191,965, filed on Nov. 15, 2018, now Pat. No. 11,501,662.
(Continued)

(51) Int. Cl.
*G09B 23/30* (2006.01)
*A61B 17/04* (2006.01)
(Continued)

(52) U.S. Cl.
CPC .......... *G09B 23/30* (2013.01); *A61B 17/0469* (2013.01); *G09B 23/285* (2013.01); *A61B 2017/00707* (2013.01)

(58) Field of Classification Search
None
See application file for complete search history.

(56) References Cited

U.S. PATENT DOCUMENTS

| 2,678,505 A | 5/1954 | Munson |
|---|---|---|
| 3,775,865 A | 12/1973 | Rowan |

(Continued)

FOREIGN PATENT DOCUMENTS

| GB | 2492115 A | 12/2012 |
|---|---|---|
| WO | WO 2004/003873 A2 | 1/2004 |

(Continued)

OTHER PUBLICATIONS

European Patent Office, The International Search Report and Written Opinion for International Application No. PCT/US2018/061275, entitled "Surgical Skills Surgical Training Model," mailed Jan. 28, 2019, 13 pgs.
(Continued)

*Primary Examiner* — James B Hull
(74) *Attorney, Agent, or Firm* — Patrick Ikehara

(57) ABSTRACT

A surgical training model can have features for training surgical suturing techniques. The training model can be formed as a sheet of simulated tissue having at least one cut with markings arranged on either side of the cut. The markings can be formed of a first layer of resilient simulated tissue material having a color that contrasts with a color of the remainder of the sheet of simulated tissue material. The sheet of simulated tissue material can have several cuts having different configurations and orientations to facilitate suturing training for a variety of tissue orientations. The sheet of simulated tissue material can further include holes positioned to be mounted to a base of a surgical training system. The sheet of simulated tissue material can be manufactured by molding a marking layer and casting a tissue layer over the marking layer.

15 Claims, 4 Drawing Sheets

Related U.S. Application Data

(60) Provisional application No. 62/586,369, filed on Nov. 15, 2017.

(51) Int. Cl.
   *G09B 23/28* (2006.01)
   *A61B 17/00* (2006.01)

(56) References Cited

U.S. PATENT DOCUMENTS

| | | | |
|---|---|---|---|
| 4,195,420 | A | 4/1980 | Fields |
| 4,386,917 | A | 6/1983 | Forrest |
| 4,596,528 | A | 6/1986 | Lewis et al. |
| 4,789,340 | A | 12/1988 | Zikria |
| 5,518,407 | A | 5/1996 | Greenfield et al. |
| 7,575,434 | B2 | 8/2009 | Palakodeti |
| 8,641,422 | B2 | 2/2014 | Francavilla |
| 9,218,753 | B2 | 12/2015 | Hoke et al. |
| 9,424,760 | B2 | 8/2016 | Ghez et al. |
| 9,520,073 | B2 | 12/2016 | Matonick et al. |
| 9,940,849 | B2 | 4/2018 | Hart et al. |
| 9,959,785 | B2 | 5/2018 | Tortola |
| 9,959,786 | B2 | 5/2018 | Breslin et al. |
| 2008/0064017 | A1 | 3/2008 | Grundmeyer, III et al. |
| 2012/0115117 | A1 | 5/2012 | Marshall |
| 2012/0115118 | A1 | 5/2012 | Marshall |
| 2014/0024004 | A1 | 1/2014 | Tvermoes et al. |
| 2014/0030682 | A1* | 1/2014 | Thilenius ............... G09B 23/30 434/219 |
| 2014/0087347 | A1* | 3/2014 | Tracy .................. G09B 23/285 434/272 |
| 2014/0212861 | A1 | 7/2014 | Romano |
| 2014/0220528 | A1 | 8/2014 | Francavilla |
| 2015/0037773 | A1 | 2/2015 | Quirarte Catano |
| 2015/0086955 | A1 | 3/2015 | Poniatowski et al. |
| 2016/0027344 | A1* | 1/2016 | Felsinger ............... B29C 39/38 264/308 |
| 2016/0071437 | A1 | 3/2016 | Hoke et al. |
| 2016/0293055 | A1 | 10/2016 | Hofstetter |
| 2017/0039892 | A1 | 2/2017 | Simoes et al. |
| 2017/0186340 | A1 | 6/2017 | Ogawa et al. |

FOREIGN PATENT DOCUMENTS

| | | |
|---|---|---|
| WO | WO 2015/177926 A1 | 11/2015 |
| WO | WO 2015/189954 A1 | 12/2015 |

OTHER PUBLICATIONS

The International Bureau of WIPO, International Preliminary Report on Patentability for International Application No. PCT/US2018/061275, entitled "Suturing Skills Surgical Training Model," dated May 28, 2020, 7 pgs.

* cited by examiner

SUTURING SKILLS SURGICAL TRAINING MODEL

CROSS-REFERENCE TO RELATED APPLICATIONS

This application is a continuation of U.S. patent application Ser. No. 16/191,965 entitled "Suturing Skills Surgical Training Model," filed Nov. 15, 2018, which claims the benefit of U.S. Provisional Patent Application Ser. No. 62/586,369 entitled "Suturing Skills Surgical Training Model" filed on Nov. 15, 2017 which is incorporated herein by reference in its entirety.

BACKGROUND OF THE INVENTION

Field of the Invention

This application is generally related to surgical training tools, and in particular, to simulated tissue structures and models for teaching and practicing various surgical techniques and procedures related but not limited to laparoscopic, endoscopic and minimally invasive surgery.

Description of the Related Art

Medical students as well as experienced doctors learning new surgical techniques must undergo extensive training before they are qualified to perform surgery on human patients. The training must teach proper techniques employing various medical devices for cutting, penetrating, clamping, grasping, stapling, cauterizing and suturing a variety of tissue types. The range of possibilities that a trainee may encounter is great. For example, different organs and patient anatomies and diseases are presented. The thickness and consistency of the various tissue layers will also vary from one part of the body to the next and from one patient to another. Different procedures demand different skills. Furthermore, the trainee must practice techniques in various anatomical environs that are influenced by factors such as the size and condition of the patient, the adjacent anatomical landscape and the types of targeted tissues and whether they are readily accessible or relatively inaccessible.

Minimally invasive surgery involves the learning of skills not inherent to open surgery. While some skills are transferrable (bimanual dexterity, steadiness, etc.) others must be acquired through deliberate practice and training. These include basic psychomotor skills such as tissue handling, needle manipulation, knot tying, etc. Such psychomotor skills are required in order for surgeons to convert to a minimally invasive practice. It is imperative for surgical trainees to demonstrate proficiency in these psychomotor skills prior to applying them to their practice in the operating room. For this reason, surgical simulation trainers and simulation models provide a valuable, safe, and effective means to develop and fine-tune minimally invasive surgical skills.

Numerous teaching aids, trainers, simulators and model organs are available for one or more aspects of surgical training. However, there is a need for model organs or simulated tissue elements that are likely to be encountered and that can be used in practicing endoscopic and laparoscopic, minimally invasive surgical procedures. In laparoscopic or minimally invasive surgery, a small incision, as small as 5-10 mm is made through which a trocar or cannula is inserted to access a body cavity and to create a channel for the insertion of a camera, such as a laparoscope. The camera provides a live video feed capturing images that are then displayed to the surgeon on one or more monitors. At least one additional small incision is made through which another trocar/cannula is inserted to create a pathway through which surgical instruments can be passed for performing procedures observed on the monitor. The targeted tissue location such as the abdomen is typically enlarged by delivering carbon dioxide gas to insufflate the body cavity and create a working space large enough to safely accommodate the scope and instruments used by the surgeon. The insufflation pressure in the tissue cavity is maintained by using specialized trocars. Laparoscopic surgery offers a number of advantages when compared with an open procedure. These advantages include reduced pain, reduced bleeding and shorter recovery times due to smaller incisions.

Laparoscopic or endoscopic minimally invasive surgery requires an increased level of skill compared to open surgery because the target tissue is not directly observed by the clinician. The target tissue is observed on monitors displaying a portion of the surgical site that is accessed through a small opening. Therefore, clinicians need to practice visually determining tissue planes, three-dimensional depth perception on a two-dimensional viewing screen, hand-to-hand transfer of instruments, suturing, precision cutting and tissue and instrument manipulation. Typically, models simulating a particular anatomy or procedure are placed in a simulated pelvic trainer where the anatomical model is obscured from direct visualization by the practitioner. Simulated pelvic trainers provide a functional, inexpensive and practical means to train surgeons and residents the basic skills and typical techniques used in laparoscopic surgery such as grasping, manipulating, cutting, knot tying, suturing, stapling, cauterizing as well as how to perform specific surgical procedures that utilize these basic skills. Simulated pelvic trainers are also effective sales tools for demonstrating medical devices required to perform these laparoscopic procedures.

One of the techniques mentioned above that requires practice in laparoscopic or minimally invasive surgery is cutting and suturing. Intracorporeal suturing and knot-tying demand high levels of precision and strong manual dexterity. Such techniques must be mastered by every surgeon interested in pursuing the minimally invasive approach. Suturing skills learned via a box trainer suture model have been previously shown to transfer to the operating room.

Key challenges faced by learners during laparoscopic suturing include psychomotor control, visuospatial orientation, knot-tying, tissue handling, needle manipulation, needle positioning, needle insertion, and assessment of suture strength and security. It is with these challenges in mind that there is a need for a model for practicing cutting and suturing. It is also desirable to have a model that not only simulates the particular anatomy but also presents the anatomy at a particular step or stage of the procedure or isolates a particular step of a procedure for the trainee to practice in a simulated laparoscopic environment. The model is then disposed inside a simulated laparoscopic environment such as a laparoscopic trainer in which it is at least partially obscured from direct visualization. A camera and monitor provide visualization to the practitioner as in real surgery. After a technique is practiced, it is furthermore desirable that such a model permits repeatable practice with ease, speed and cost savings. In view of the above, it is an object of this invention to provide a surgical training device that realistically simulates an anatomy, isolates such anatomy and presents such an anatomy at a particular stage or step of a procedure that also enables repeatable practice.

It has been demonstrated that the use of simulation trainers greatly enhances the skill levels of new laparoscopists and are a great tool to train future surgeons in a non-surgical setting. There is a need for such improved, realistic and effective surgical training models. Laparoscopic suturing is a method of enclosing lacerations, incisions or cuts made within the tissues and organs within the abdominal cavity. Depending on the surgical procedure being performed the suturing can occur on a variety of anatomical structures. Laparoscopy and specifically laparoscopic suturing is a surgical skill in which there is a need for a model that will allow this skill to be learned and practiced. There is a need for this training to be performed on a physical model that allows for the practicing surgeon or surgical resident to have haptic feedback for tissue reactions. This haptic feedback is important for a trainee to learn the appropriate level of force to apply on tissue being sutured.

SUMMARY OF THE INVENTION

In certain embodiments, a surgical training model for training suturing techniques is provided. The model comprises a sheet of simulated tissue material defining a suture pad. The sheet comprises a first layer of simulated tissue material, a second layer of simulated tissue material, and at least one cut. The first layer of simulated tissue material is defined by a plurality of markings. The second layer of simulated tissue material is cured to the first layer of simulated tissue material. The at least one cut is formed in the sheet of simulated tissue material. The markings of the first layer are arranged on either side of the at least one cut.

In certain embodiments, a surgical training model for training suturing techniques is provided. The surgical training model comprises a sheet of simulated tissue material defining a suture pad. The sheet has an upper surface and a lower surface defining a thickness therebetween. The sheet comprises a first cut, a first plurality of markings, a second cut, a second plurality of markings, a third cut, and a third plurality of markings. The first cut extends through the sheet of simulated tissue material from the upper surface to the lower surface. The first plurality of markings is arranged on either side of the first cut. The second cut extends through the sheet of simulated tissue material from the upper surface to the lower surface. The second plurality of markings is arranged on either side of the second cut. The third cut extends through the sheet of simulated tissue material from the upper surface to the lower surface. The third plurality of markings is arranged on either side of the third cut.

In certain embodiments, a method of making a surgical training model for training suturing techniques is provided. The method comprises providing a mold, providing a marking mold, applying wet silicone to the marking mold, positioning the marking mold, and casting wet silicone. The mold comprises a well sized and shaped to correspond to the surgical training model. The marking mold is sized to fit inside the well of the mold. The marking mold includes a plurality of holes formed therein. The wet silicone enters the holes of the marking mold during applying wet silicone onto the marking mold. The marking mold is positioned within the well of the mold during positioning the marking mold. Wet silicone is cast over the marking mold positioned within the mold during casting wet silicone.

DETAILED DESCRIPTION OF THE INVENTION

Figure 2:
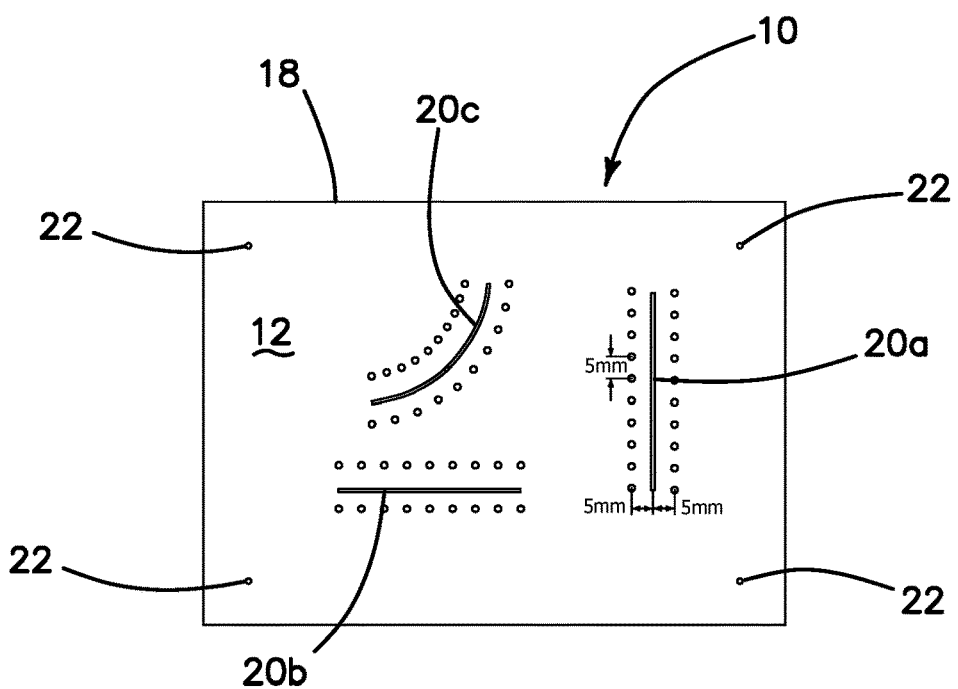
FIG. 2 illustrates a top view of the suture pad of FIG. 1.

FIG. 2 illustrates an embodiment of suture pad 10. In the illustrated embodiment, the suture pad 10 is a sheet of simulated tissue material having an upper surface 12 and a lower surface 14 defining a thickness therebetween. The thickness is substantially uniform across the pad and approximately 5 millimeters. The thickness and properties of the pad 10 are ideal to simulate tissue re-approximation with skilled laparoscopic suturing. The suture pad 10 has a perimeter 18 which, in one variation, defines a rectangular shape as shown in FIG. 2. The perimeter shape can be any suitable shape. The suture pad 10 is made of silicone, low durometer silicone or other suitable polymeric material such as KRATON® or thermoplastic elastomer. The low durometer allows for the suture pad 10 to have the haptic feedback to simulate soft tissue. Material is chosen to simulate the elasticity, needle resistance, and handling characteristics of live tissue that may be encountered in the operating room. The material can also be other rubber-like materials, or thermoset plastic materials that have a soft durometer.

In one variation, the suture pad 10 includes a layer of fabric or mesh embedded within the thickness of the pad. The fabric or mesh is preferably a 2-way or 4-way stretch material such as stretch nylon or spandex or a stretch nylon/spandex blend mesh or fabric. The fabric or mesh material is stretchable and porous and weighs approximately 79 grams per square yard. The suture pad 10 may include, in addition to or in lieu of the mesh or fabric material, a reinforcement material, fiber, dye and surface texturing. The upper and lower surfaces 12, 14 of FIG. 2 are smooth and without surface texturing. The suture pad 10 is flexible and can stretch. The mesh, fabric, fiber or other filler material provides reinforcement to the silicone such that the sheet can hold a suture or be stretched without tearing when being manipulated or connected to a base. In order to train users respect for tissue techniques, the mesh, fabric, fiber or other filler material may be omitted to create a less resilient and more sensitive pad that is more easily torn when manipulated, thereby, increasing the difficulty of the practice.

The suture pad 10 includes at least one cut 20. The cut 20 is a simulated laceration formed in the suture pad 10. FIG. 2 illustrates three cuts 20a, 20b, 20c in the suture pad 10. Typically, a cut 20 extends from the upper surface 12 to the lower surface 14 across the thickness of the pad 10. A partial cut 20 that does not extend across the entire thickness may also be employed for one or more of the cuts. The cut 20 may be any shape. For example, the cut 20 may be a straight line or curve. The curve may be a closed curve or an open curve and multiple cuts 20 may be employed in conjunction with each other to define a suture line of varying difficulty or to define varying practice orientations. Lacerations are strategically placed in a variety of orientations so that the learner may adapt their skillset to various tissue orientations encountered in the operating room. The suture pad 10 in FIG. 2 includes two straight cuts 20a, 20b and one curved cut 20c oriented with respect to each other to provide various practice orientations. The two straight cuts 20a, 20b are shown to be perpendicular to each other but the invention is not so limited. The two cuts 20 can be at any angle with respect to each other or mimic actual suture lines associated with a particular organ or otherwise encountered in real surgery or designed to teach a particular skill, train hand dominance, practice different suture run styles and the like. Each cut 20 is substantially perpendicular to the upper and lower surfaces 12, 14 and includes two oppositely disposed inner surfaces that face each other.

When approximated, the two inner surfaces of a cut 20 are in close juxtaposition and the cut may be difficult to discern by the user. When mounted on a base, the suture pad 10 may be stretched and, as a result, the cut 20 may open up and define a greater space between the inner surfaces which would require greater force to approximate the inner surfaces while suturing. In the variation shown in FIG. 2, the first cut 20a is approximately 4.0 centimeters in length, the second cut 20b is approximately 3.5 centimeters in length and the third cut 20c is approximately 4.0 centimeters in length. FIG. 2 is not drawn to scale. The cuts 20 are pre-formed and, in one variation, no cuts 20 are pre-formed allowing the user to make the incision as part of the skills training exercise. The suture pad 10 may further include small pre-formed apertures 22 near the perimeter sized and configured for mounting the pad 10 onto a base. The variation in FIG. 2 includes four apertures 22 in each corner of the rectangular pad.

The suture pad 10 further includes a plurality of markings 24 arranged on either side of a cut 20. The markings 24 are arranged in a first row 26 along the length and on one side of the cut 20 and in a second row 28 along the length and one the opposite side of the cut 20. The first row 26 of markings 24 are directly opposite the second row 28 of markings 24. The markings 24 in each row are equally spaced apart from each other. In particular, each marking 24 is spaced from each other by approximately 5 millimeters. The center-to-center distance between each marking in the same row is approximately 5 millimeters. The distance between the two rows 26, 28 across the laceration is approximately 10 millimeters. Each row is approximately 5 millimeters away from the laceration. In the case of a cut 20 having a curved shaped, the markings 24 on the inside of the curve will naturally be spaced closer together relative to the markings 24 on the outside of the curve as can be seen in FIG. 2. The number of markings 24 along a laceration will vary and depends on the length of the cut 20. For example, a cut 20 that has a length of approximately 4 millimeters will have 10 markings in each row for 9 suture runs (10 including knot) for a total of 20 markings 24. A cut 20 that has a length of approximately 3.5 millimeters will have 9 markings in each row for 8 suture runs (9 including knot) for a total of 18 markings 24. The knot and final suture pass including the markings 24 at the ends of the cut 20 will extend slightly beyond the laceration length. The marking dots serve as precision targets through which the end user should drive the needle. The distance between each marking pairing creates a standard distance for a suture run to be made along with a standard distance between a suture bite to close the incision.

In one variation, the markings 24 are small circular dots having a diameter of approximately 1/16 inch. The markings 24 are not limited to having a circular shape. For example, the markings 24 may be X-shaped, filled circles, empty circles, boxes, star-shaped or any suitable shape that communicates a target with substantial precision for the length and size of the cut. The markings 24 are dark in color or any suitable color that provides a visible contrast against the color of the pad 10 to the user. The markings have a color that creates a high color contrast with the silicone portion of the suture pad 10 containing the pre-made incisions. Color contrasts between each part of the suture pad 10 are black dot pairings with a light, flesh-tone colored rectangular footprint.

The markings 24 may be applied to the pad 10 in any number of suitable ways. For example, the markings 24 may be drawn in ink, stamped, printed and the like. The markings 24 may be applied to the upper surface 12 or just beneath the upper surface in a visible manner. For example, the markings may be printed on the embedded fabric layer or on an intermediate silicone layer prior to casting a final silicone layer and visible through transparent or translucent silicone in which it is embedded. Another method of applying the markings 24 will now be described.

Figure 3:
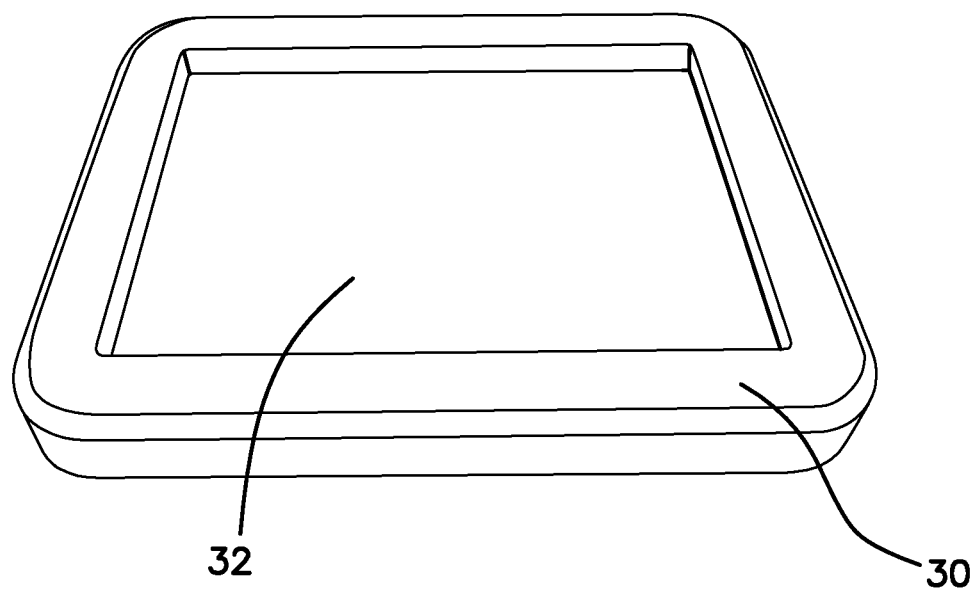
FIG. 3 illustrates a top perspective view of a suture pad mold.
Figure 4:
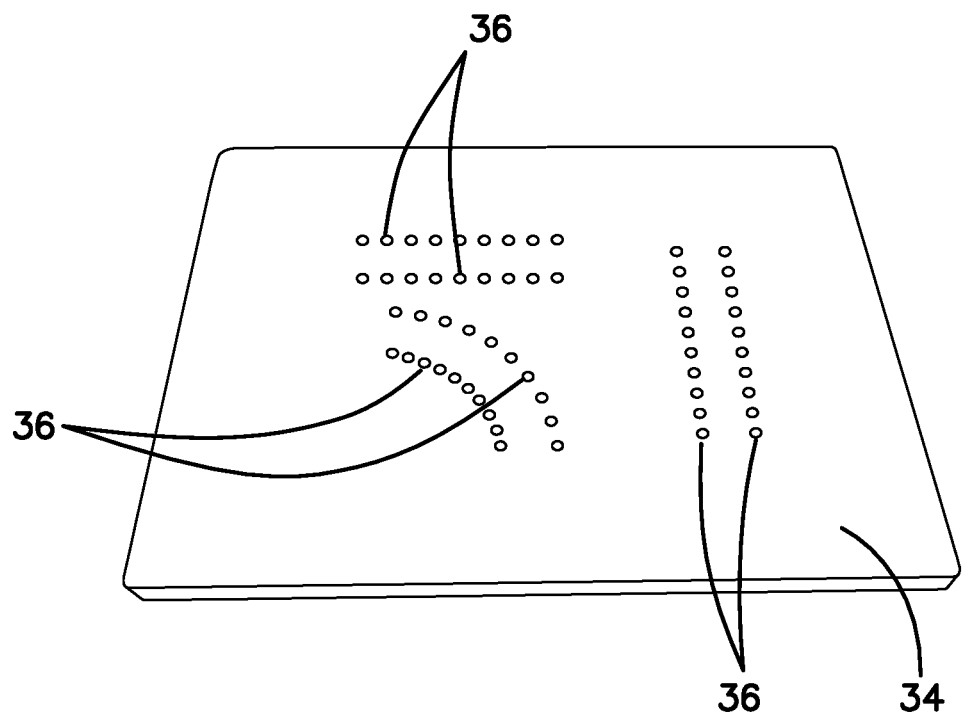
FIG. 4 illustrates a top perspective view of a marking mold.
Figure 5:
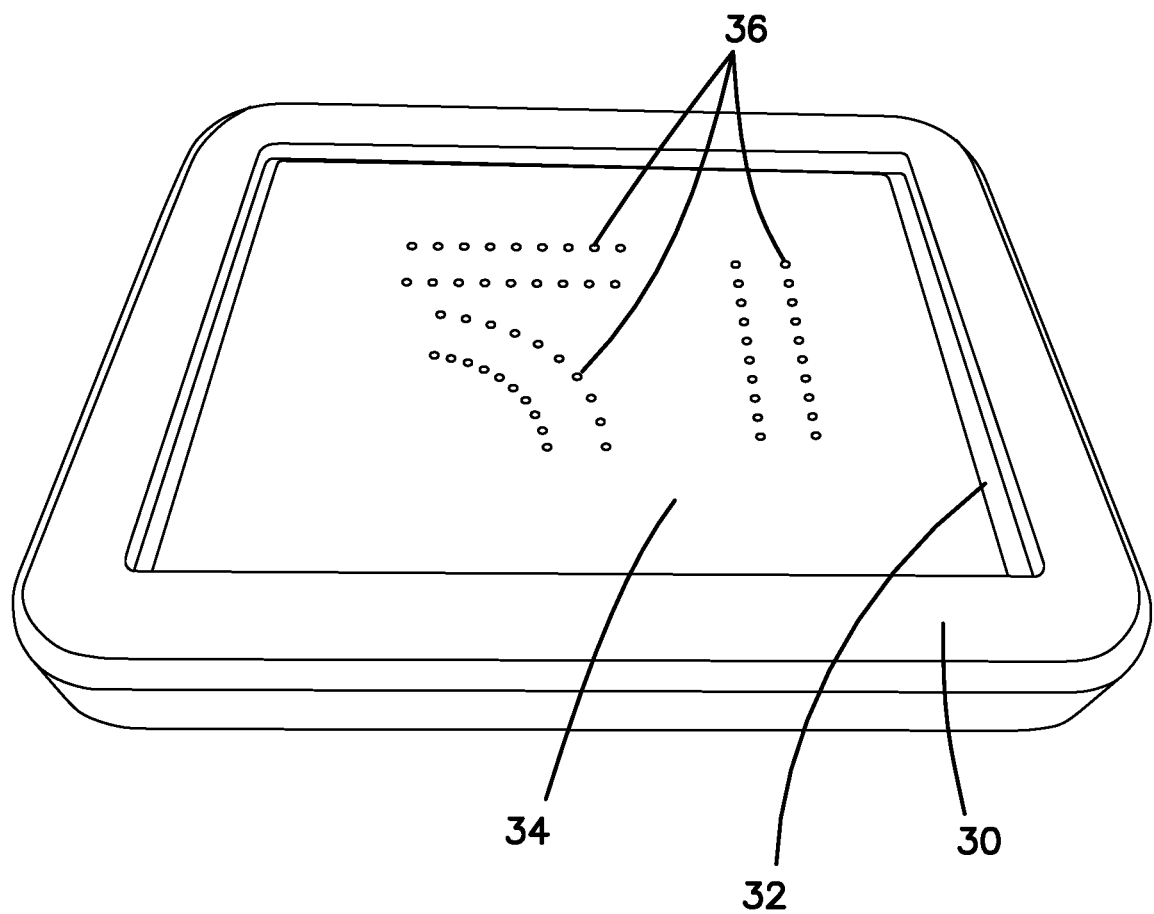
FIG. 5 illustrates a top perspective view of a marking mold inside a well of the mold of FIG. 3.

Turning now to FIG. 3, there is shown a mold 30. The mold 30 includes a well 32 that is sized and shaped to correspond to the desired size and shape of the suture pad 10. A marking mold 34 shown in FIG. 4 is provided. The marking mold 34 includes a plurality of holes 36 formed in the marking mold 34. The holes 36 are sized and shaped to correspond to the desired size and shape of the resulting markings 24 to be formed on the pad 10. The marking mold 34 is sized to fit inside the well 32 of the mold 30 as shown in FIG. 5. FIG. 5 shows the marking mold 34 placed inside the well 32 of the mold 30. In this method of making a suture pad 10 with markings 24, wet silicone having a dark/contrast color to the color of the pad 10 is applied onto marking mold 34 such that the wet silicone enters each of the holes 36. Excess wet silicone is wiped away and the silicone inside the holes 36 is allowed to cure. The marking mold 34 with the cured silicone inside the holes 36 is then placed/nested into the well 32 of the mold 30 and wet flesh-tone silicone for the pad is then casted into the well 32 on top of and or over the marking mold with the cured black colored silicone and allowed to cure. As the uncured silicone of the pad 10 cures it is adheres itself to the cured silicone inside the holes 36. In one variation, the flesh-tone layer is not filled up to the top of the mold in order to allow a mesh layer or markings to be added after the first layer of flesh-toned silicone has cured. After a mesh/fabric/reinforcement and or markings layer is added, more flesh-toned silicone is added forming a second layer of flesh-tone silicone to complete the thickness of the suture pad. The silicone-to-silicone adhesion properties allow the flesh tone layers to adhere together, therefore, encapsulating the mesh layer in between. The mesh layer serves as a reinforcement to hold a variety of sutures that are pulled with varying forces. The second layer of silicone may be transparent and or translucent so that any markings may be seen therethrough. After the silicone is cured, the pad is removed from the mold 30 with the markings 24 adhered. If markings are embedded within the layer, printed on a fabric layer or first layer of silicone, the marking mold is not employed. The adhesion properties of silicone allow the silicone flesh tone layer to be adhered to the black dots. Silicone adhesive can be additionally used on top of each black dot pairing to further reinforce the adhesion between the dots and the flesh-tone layer. The resulting markings 24 are raised with respect to the upper surface 12. Once all the silicone layers are cured, the suture pad 10 is centered on a cutting die that cuts out the incisions in the center of each dot paring. The lengths of the incisions may vary. In one variation, the lengths are at least 4.0 cm and 3.5 cm in order to capture multiple suture runs, 9 and 8 runs, respectively. An additional run for each length can be made in order to accommodate the knot.

Figure 6:
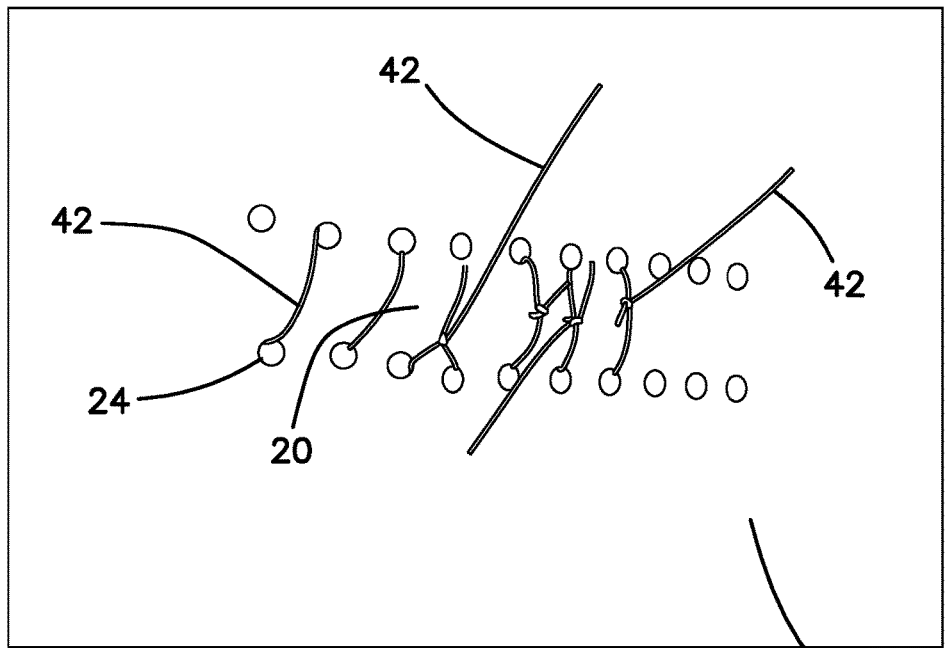
FIG. 6 illustrates a top perspective view of a suture pad with sutures.
Figure 7:
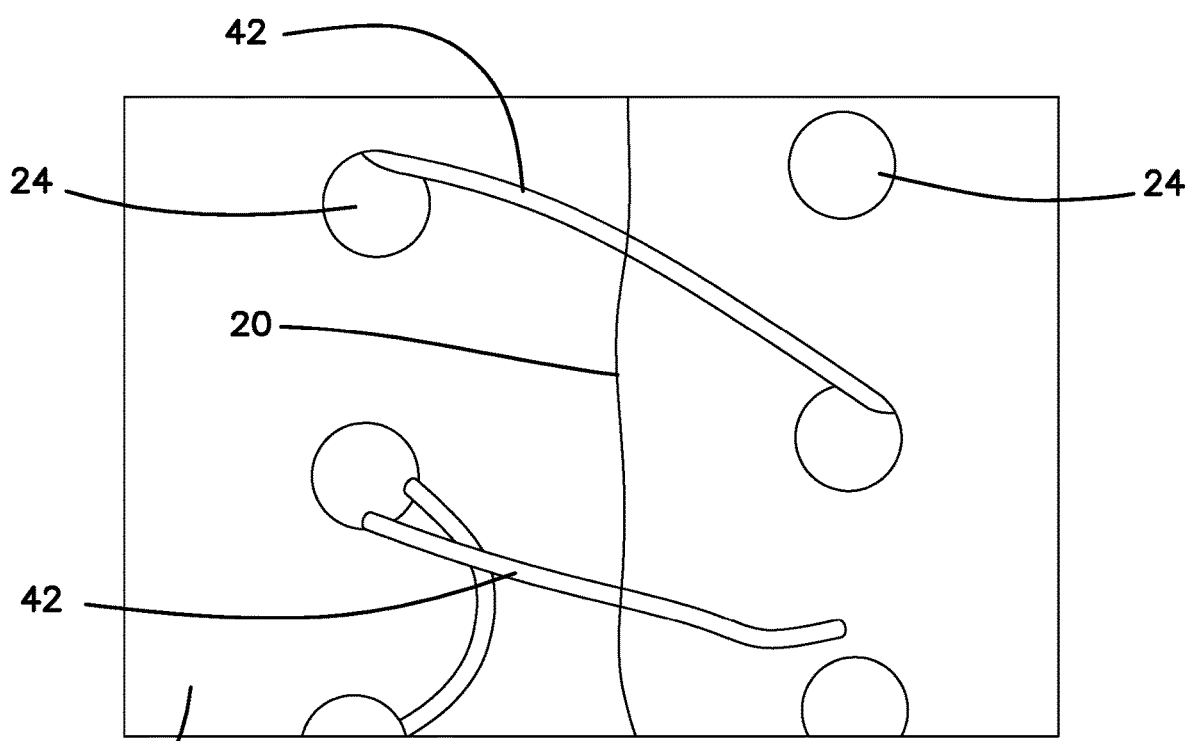
FIG. 7 illustrates a top perspective view of a suture pad with sutures.

The markings 24 serve as targets for passing a suture and are intended to guide the learner toward ideal needle insertion points around the laceration. The user will practice suturing across the laceration by passing the suture needle and suture through the center of the marking 24. An assessment of a user's skills is easily performed by observing whether the suture needle and suture has passed through the marking, its center or not. Hence, the suture pad 10 provides a tool for users to learn, practice and improve their suturing techniques. The markings 10 also serve as a means for easily evaluating the user's skills. The marking placements allow for reflective assessment of suture performance based on target accuracy. An exemplary suture 42 placement is shown in FIG. 6. FIG. 7 illustrates a suture pad after completed suture practice. As can be seen in FIG. 7, the suture has hit and missed the target markings 24. In certain suture practice exercises, a typical 2-O coated vicryl (polyglactin) dyed suture approximately 70 cm in length can be used and cut to four times the laceration length for ideal handling with the suture pad 10. In other exercises, a variety of suture and needle types and lengths can be utilized with the suture pads described herein. The user can employ a simple continuous suture run style and perform suture on all three lacerations/orientations.

The flesh tone portion of the suture pad 10 can be textured. The textured surface allows the suture pad 10 to be easily grasped and manipulated. The mesh layer can be removed in order to simulate training on more fragile tissue. The durometer used for the flesh tone portion of the suture pad 10 can be made from a mixture of at least two different silicone durometers, a low and high, in order to get a realistic haptic feedback response that is similar to tissues within the abdominal cavity. The rectangular footprint of the suture pad 10 can be re-shaped to variety of sizes or geometries if a particular procedure involving suturing is being trained. The incisions 20 can include a straight incision that is angled. The suture pad can include any number of incisions. The incision lengths can also be less than 4.0 cm or 3.5 cm. Colors of the suture pad 10 are not limited to flesh tone and black. The color of the targets 24 and the underlying silicone layer, however, should provide a contrasting difference from one another so that the end user is able to distinguish between each feature.

In another variation, the markings 24 are recessed into the suture pad 10 rather than extended outward above the upper surface 12. In another variation, the markings 24 are stamped with different inks such as markers or stamped with silicone pigment or silicone inks. In one variation, the markings 24 are holes in the suture pad 10 having any suitable target shape. The pairings or rows of markings 24 can be a combination of the differently shaped markings in order to, for example, provide a further challenge to the training by requiring the user to run the suture through only the corresponding geometrical shape pairings. In another variation designed to train specifically on the suture width, the dots can be represented as rectangular features on either side of the incision. Also, to increase the number of uses for the suture pad 10, running sutures can be made on open spaces in between each dot pairing.

Figure 1:
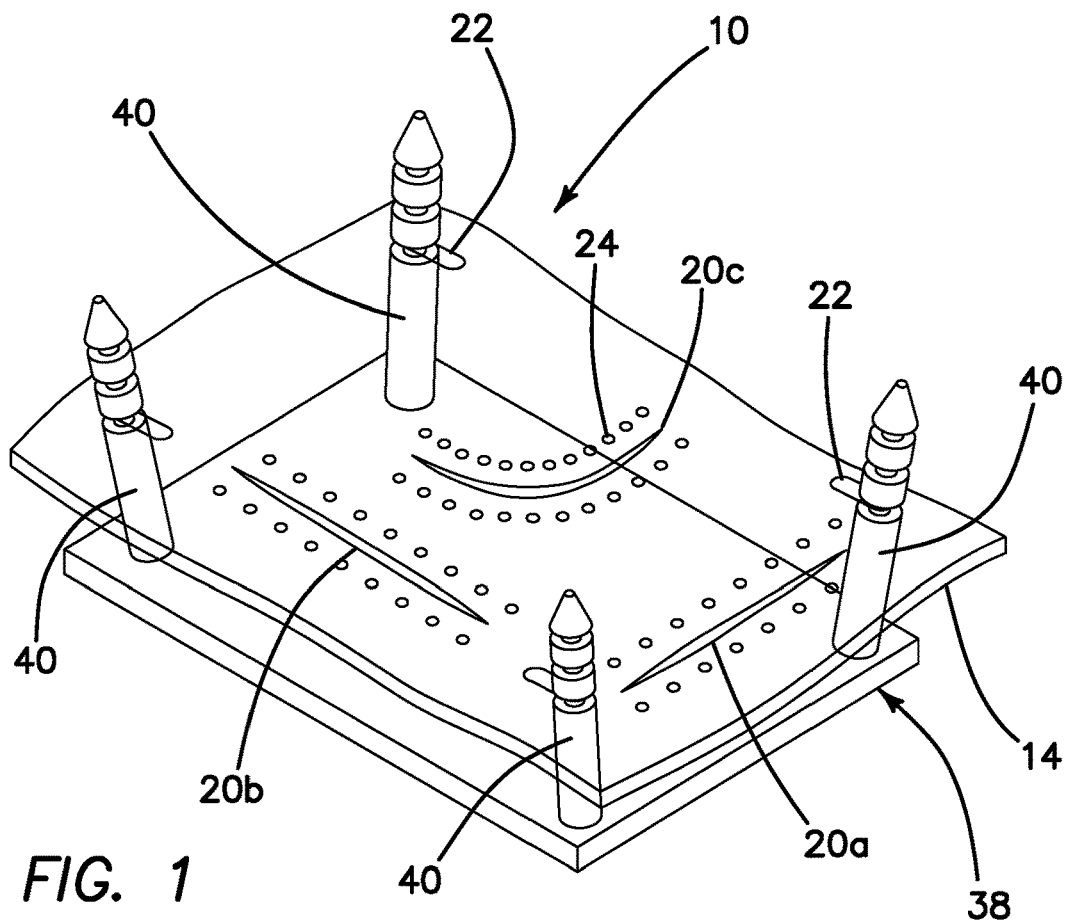
FIG. 1 illustrates a top perspective, partially transparent view of an embodiment of suture pad mounted on posts of a base.

The suture pad 10 of the present invention is typically mounted onto a base 38 as shown in FIG. 1. The base 38 is a platform that serves as a bottom support for the suture pad 10 and it is sized and configured such that the base 38 and pad 10 do not tip over. The platform is made of any material such as metal or plastic. The base 38 is of sufficient heft to maintain its stability while being manipulated by a user. The base 38 includes posts 40. Generally, four posts 40 are connected to the base 38. Each post 38 is elongate and cylindrical in shape having a proximal end connected to the base 38 and a distal end that extends upwardly from the base 38. In one variation, the distal end includes a tapered section that terminates at a blunt tip surface so as to not injure a user but is sharp enough to puncture holes in the suture pad 10 for mounting it onto the base 38. Each post 40 includes at least one circumferential notch that extends radially inwardly configured to receive the thickness of the pad 10 within the notch so as to prevent the pad 10 from sliding up or down the post 40. An exemplary base is described in U.S. patent application Ser. No. 14/037,005 entitled "Surgical training model for laparoscopic procedures" filed on Sep. 25, 2013 and is incorporated herein by reference in its entirety.

The suture pad 10 is connected to the posts 34 and in essence suspended from the base by a distance. The suture pad 10 is mounted in tension being slightly stretched between and connected to the posts 40 as shown in FIG. 1. The tension of the suture pad 10 may be adjusted by angulating the posts 40 or by stretching and piercing the suture pad 10 in locations closer together along the simulated tissue portion. The placement of the suture pad 10 onto the base advantageously allows for additional manipulation of tissue orientation. The use of silicone for the suture pad allows it to be flexible such that, when it is assembled on the base, the pad can be oriented in the vertical position or horizontal position and any angle in between. This creates multiple planar views for the suture pad to allow for spatial challenge training for this skill.

The suture pad 10 may be employed by itself or mounted on the base 38. In either case, the suture pad 10 by itself or mounted on the base 38 may be placed inside a surgical training device for the practice of suturing in a laparoscopic environment. The surgical training device is typically configured to mimic the torso of a patient such as the abdominal region. An example of a surgical training device is described in U.S. Pat. No. 8,764,452 entitled Portable Laparoscopic Trainer incorporated herein by reference in its entirety. The surgical training device provides a body cavity substantially obscured from the user and configured for receiving the suture pad inside the cavity. The body cavity and the suture pad disposed therein are accessed via a tissue simulation region in the trainer that is penetrated by the user employing laparoscopic devices. The surgical trainer is a useful tool for teaching, practicing and demonstrating various surgical procedures and their related instruments in simulation of a patient undergoing a surgical procedure. Surgical instruments are inserted into the cavity through the tissue simulation region as well as through pre-established apertures in the top cover. The suture pad 10 may be connected to the trainer with clips. If a base 38 is employed, it may be retained with a patch of hook-and-loop type fastening material (VELCRO®) affixed to the base and to the floor of the trainer. A video display monitor provides the user with a view of the mock surgical field inside the cavity of the trainer via a camera such as an endoscope.

In use, a user will mount at least one suture pad 10 onto the posts 40 connected to the base 38. If the suture pad 10 includes preformed apertures 22 then mounting the suture pad 10 includes placing the apertures 22 over each post 34 and sliding the simulated tissue portion 36 to rest within one of the at least one notches 42 formed in the post 34. The suture pad 10 is mounted on all four posts 40. Fewer posts may be employed to suspend the suture pad 10. The notches advantageously permit the entire suture pad 10 to be mounted at an angle such that one side or at least one corner of the suture pad 40 is mounted on a higher or lower notch relative to the other corners and posts. If the suture pad 10 is not provided with preformed apertures 22, the tapered distal ends of the posts 40 can be used to puncture apertures 22 anywhere into the pad 10. Hence, the tension in the suture pad 10 can be selected by the user when the user mounts the suture pad 10 onto the posts 40. For example, when the suture pad 10 is mounted by piercing an aperture 22 into the suture pad 10, it can then be selectively stretched making the suture pad 10 as tense or loose as the user wishes before piercing at least a second aperture 22 to mount the suture pad 10 on another post 40 and so forth. The fabric reinforced silicone material prevents the aperture 22 from propagating.

The suture pad 10 provides a realistic platform for presenting simulated suturable tissue for training in a laparoscopic environment. As the clinician practices certain techniques such as cutting and suturing, the clinician will use certain instruments such as graspers, cutters, suture needles, sutures, laparoscopes, endoscopes, trocars and the like. When the suture pad that is supported on the posts is contacted with such instruments, the simulated tissue structure will give and flex under the force, deflecting a certain degree depending upon the tension with which it is mounted. This dynamism of the suture pad advantageously mimics real live tissue that gives way, moves and flexes upon manipulation in real life. Also, cutting and suturing feels differently when performed on a suture pad that is suspended, that is in tension and that allows for a certain amount of deflection. These simulation advantages are provided by the suture pad 10 of the present invention and are particularly useful when practicing laparoscopic surgical techniques that allow the user to fine tune depth perception and tissue manipulation skills while suturing, cutting and puncturing in a simulated laparoscopic environment. The present invention provides a model for guided suture placement for the development of laparoscopic suturing skillsets through deliberate practice.

The suture pad has a reaction that simulates soft tissue found within the abdominal cavity. Since this pad allows for laparoscopic suture training, the suture pad 10 can be grasped and manipulated with laparoscopic instruments such as laparoscopic scissors, graspers, and Maryland dissectors. Additionally, this pad is tough enough to hold various types of sutures that could be encountered within a surgical procedure. Although the suture pad 10 is tough enough to withstand suture, it is also fragile enough such that the strength and force required to create a suture is similar to tissue reaction encountered during laparoscopic procedures. Since suturing is the laparoscopic target skill for the suture pad, the suture pad allows for multiple suture orientations to be learned and practiced. In addition, the suture pad allows for a laparoscopic running suture, such as a simple continuous suture, to be made. To accommodate multiple planar views, the suture pad is able to be fixed on the base to have a front or angled face orientation. In order to maximize learning and training, the suture pad contains multiple lacerations or incisions to enable multiple suture runs. To allow for complete training of the suture skill, the suture pad allows the end user to create a knot and final suture. The suture pad has multiple lacerations or incision orientations to be sutured to facilitate learning multiple suturing orientations. This allows for visual and movement challenges in difficulty levels for the trainee. Additionally, the suture pad permits the practicing surgeon or surgical resident to demonstrate dexterity and precision through their movement of suturing. Having a suture pad that contains precision targets for suturing allows the trainee to practice on their laparoscopic dexterity. Additionally, the suture pad allows for the targets to serve as a metric for the trainee's dexterity of laparoscopic suturing that is assessable. To allow for objective assessment, the present suture pad has targets that are well-defined and consistent in spacing between the laceration or incision and the spacing between each consecutive pair of precision target markings on the pad. The spacing between the targets is selected to facilitate a strong suture placement. Deviation from suture targets may result in suture that lacks integrity and may fail to re-approximate tissue fully. Furthermore, material properties of the suture pad are such that the user can practice applying the appropriate amount of tension on their suture. If the user runs suture with too much force or tension, the tissue will cinch, or over-approximate. If the suture is run too loose, the user will identify that the laceration remains open, and tissue fails to re-approximate.

While certain embodiments have been particularly shown and described with reference to exemplary embodiments thereof, it will be understood by those of ordinary skill in the art that various changes in form and details may be made therein without departing from the spirit and scope thereof as defined by the following claims.

What is claimed is:

1. A surgical training model for training suturing techniques, the surgical training model comprising:
   a sheet of simulated tissue material defining a suture pad, the sheet comprising:
   a first layer of simulated tissue material,
   a second layer of simulated tissue material at least partially attached on top of the first layer of simulated tissue material,
   a plurality of markings positioned beneath an upper surface of the second layer and are visible through the upper surface of the second layer, the plurality of markings are pre-determined geometric shapes configured to serve as targets through which a user should insert a needle during a suturing process, and
   at least one cut, wherein the at least one cut extends through the first layer and the second layer, and wherein the plurality of markings are arranged in rows on each side of the at least one cut.

2. The surgical training model of claim 1, wherein one or more of the plurality of markings are small circular filled dots.

3. The surgical training model of claim 1, wherein one or more of the plurality of markings are colored to provide a visible contrast with a color the first layer and/or the second layer of simulated tissue material.

4. The surgical training model of claim 1, wherein one or more of the plurality of markings are printed on a fabric layer positioned between the first layer and the second layer.

5. The surgical training model of claim 1, wherein one or more of the plurality of markings are printed on an intermediate silicone layer positioned between the first layer and the second layer.

6. The surgical training model of claim 1 further comprising a reinforcement layer configured to hold sutures.

7. The surgical training model of claim 6, wherein the reinforcement layer comprises a mesh layer.

8. The surgical training model of claim 1, wherein the first layer and the second layer are adhered together using a silicone-to-silicone connection.

9. The surgical training model of claim 1, wherein two or more of the plurality of markings are grouped together and have the same geometric shape.

10. The surgical training model of claim 1, wherein each of the plurality of markings are arranged with a center-to-center distance of 5 millimeters from each other.

11. The surgical training model of claim 1, wherein the rows on each side of the at least one cut are spaced 5 millimeters from the at least one cut.

12. The surgical training model of claim 1, wherein the at least one cut extends at least partially through only the second layer.

13. The surgical training model of claim 1, wherein the at least one cut extends through the second layer and at least partially through the first layer.

14. The surgical training model of claim 1, wherein each of the plurality of markings have a diameter of 1/16 inch.

15. A surgical training model for training suturing techniques, the surgical training model comprising:
   a sheet of simulated tissue material defining a suture pad, the sheet comprising:
   a first layer of simulated tissue material having an upper surface and a lower surface,
   a second layer of simulated tissue material having an upper surface and a lower surface adjacent to the upper surface of the first layer of simulated tissue material,
   a plurality of markings disposed between the upper surface of the second layer of simulated tissue material and the lower surface of the first layer of simulated tissue material, the plurality of marking being visible beneath the upper surface of the second layer of simulated tissue material, and the plurality of markings are filled circles configured to serve as targets through which a user should insert a needle during a suturing process, and
   at least one cut disposed between the plurality of markings and extending through the upper and lower surface of the second layer of simulated tissue material, wherein the plurality of markings are arranged in rows on each side of the at least one cut.

* * * * *